(12) United States Patent
McNair

(10) Patent No.: US 10,354,751 B1
(45) Date of Patent: Jul. 16, 2019

(54) COMPUTERIZED SYSTEMS AND METHODS FOR PROVIDING MOBILE-DEVICE UPDATES OF ELECTRONIC HEALTH RECORDS

(71) Applicant: CERNER INNOVATION, INC., Kansas City, KS (US)

(72) Inventor: Douglas S. McNair, Leawood, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

(21) Appl. No.: 15/395,330

(22) Filed: Dec. 30, 2016

Related U.S. Application Data

(63) Continuation of application No. 14/841,093, filed on Aug. 31, 2015, now Pat. No. 9,633,169, which is a
(Continued)

(51) Int. Cl.
*G06K 7/10* (2006.01)
*G16H 10/60* (2018.01)
(Continued)

(52) U.S. Cl.
CPC ......... *G16H 10/60* (2018.01); *G06K 7/10861* (2013.01); *G16H 50/20* (2018.01); *H04L 63/08* (2013.01)

(58) Field of Classification Search
CPC .... G06Q 20/32; G06Q 20/3274; G06Q 50/22; G06Q 50/24; G06F 19/322; G06F 19/345;
(Continued)

(56) References Cited

U.S. PATENT DOCUMENTS 6,047,257 A * 4/2000 Dewaele .............. G03B 42/047
250/581
7,546,954 B2 6/2009 Longacre, Jr. et al.
(Continued)

OTHER PUBLICATIONS

Notice of Allowance received for U.S. Appl. No. 13/738,277 dated May 18, 2015, 10 pages.

*Primary Examiner* — Seung H Lee
(74) *Attorney, Agent, or Firm* — Shook, Hardy & Bacon L.L.P.

(57) ABSTRACT

A system, method, and computer-readable media are provided for facilitating clinical decision making, and in particular, decision making based on a third party's clinical situation by determining and providing useful, up-to-date information, such as patient-related information to a decision maker. In one embodiment, a user first identifies an information item concerning a patient. Based on that item, a set of related information items is determined and prioritized, and a reference pointer, which identifies the set of related information, is generated. The reference pointer is communicated to the user's mobile device. Subsequently, the user's mobile device requests information from the set of information items associated with the reference pointer, and provides information authorization information. Following authentication of the user's credentials, updates of information from the set of information items is communicated to the user's mobile device as they become available.

13 Claims, 10 Drawing Sheets

Related U.S. Application Data continuation of application No. 13/738,277, filed on Jan. 10, 2013, now Pat. No. 9,141,726.

(60) Provisional application No. 61/585,102, filed on Jan. 10, 2012.

(51) Int. Cl.
    *H04L 29/06*     (2006.01)
    *G16H 50/20*     (2018.01)

(58) Field of Classification Search
    CPC .......... G06F 21/6245; G06F 17/30943; G06K 7/10861; H04L 63/08; G16H 10/60; G16H 50/20
    USPC ...................................................... 235/375
    See application file for complete search history.

(56) References Cited

U.S. PATENT DOCUMENTS

| | | | |
|---|---|---|---|
| 7,698,269 | B2 | 4/2010 | Zhou et al. |
| 7,698,347 | B2 | 4/2010 | Vidya Sagar |
| 7,992,773 | B1 | 8/2011 | Rothschild |
| 8,054,177 | B2 | 11/2011 | Graves et al. |
| 2001/0049274 | A1 | 12/2001 | Degraeve |
| 2002/0111830 | A1 | 8/2002 | Tahan |
| 2002/0152239 | A1* | 10/2002 | Bautista-Lloyd ............ G06F 17/30899 715/234 |
| 2003/0074328 | A1 | 4/2003 | Schiff et al. |
| 2003/0182414 | A1* | 9/2003 | O'Neill ................... G06F 8/654 709/223 |
| 2004/0153344 | A1 | 8/2004 | Bui et al. |
| 2006/0229918 | A1 | 10/2006 | Fotsch et al. |
| 2006/0255143 | A1 | 11/2006 | Ehrhart |
| 2007/0043879 | A1 | 2/2007 | Vidya Sagar |
| 2007/0083535 | A1* | 4/2007 | Zilliacus ........... G06F 17/30905 |
| 2007/0136202 | A1 | 6/2007 | Noma et al. |
| 2007/0136279 | A1 | 6/2007 | Zhou et al. |
| 2007/0138253 | A1 | 6/2007 | Libin et al. |
| 2007/0282633 | A1 | 12/2007 | Haider et al. |
| 2008/0021834 | A1* | 1/2008 | Holla .................... G06F 19/322 705/51 |
| 2008/0126729 | A1 | 5/2008 | Cai et al. |
| 2008/0208897 | A1 | 8/2008 | Lew et al. |
| 2009/0037224 | A1 | 2/2009 | Raduchel |
| 2009/0069000 | A1* | 3/2009 | Kindberg ................ G06F 19/00 455/414.3 |
| 2009/0222353 | A1 | 9/2009 | Guest et al. |
| 2010/0042824 | A1 | 2/2010 | Lee et al. |
| 2011/0112850 | A1 | 5/2011 | Beraja et al. |
| 2011/0276349 | A1 | 11/2011 | Huang et al. |
| 2011/0295078 | A1 | 12/2011 | Reid et al. |
| 2012/0041774 | A1 | 2/2012 | Schmitt et al. |
| 2012/0295078 | A1 | 11/2012 | Kondo et al. |

\* cited by examiner

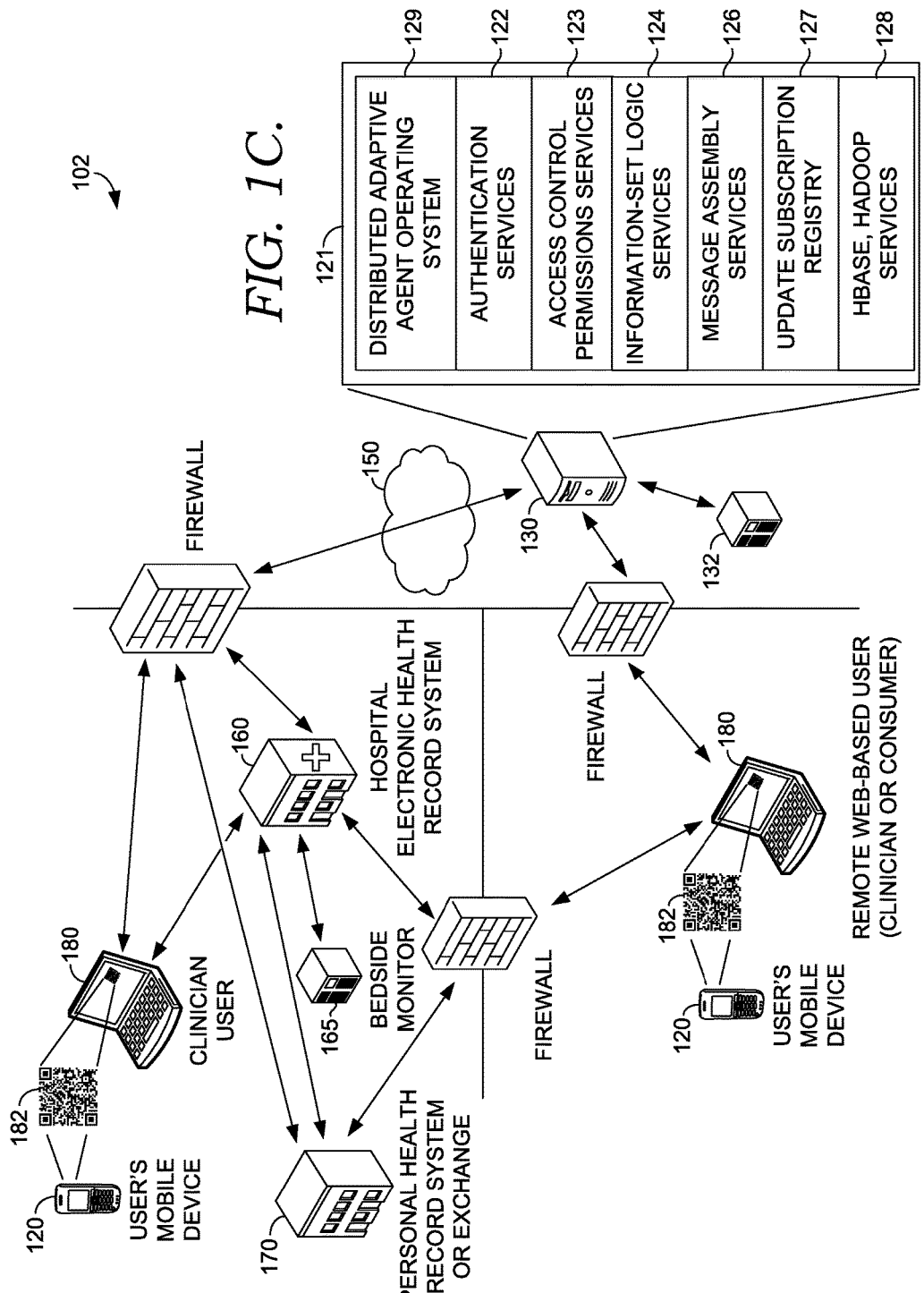

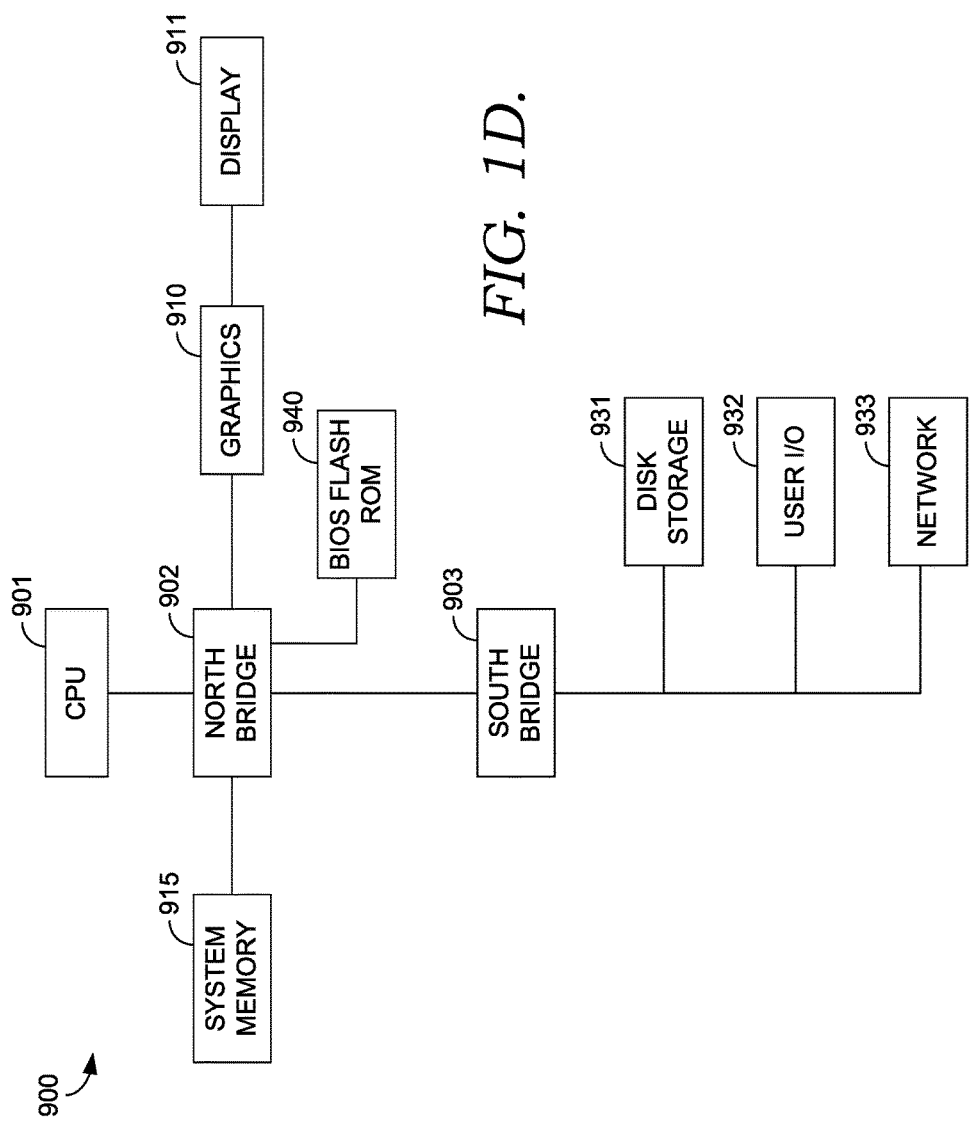

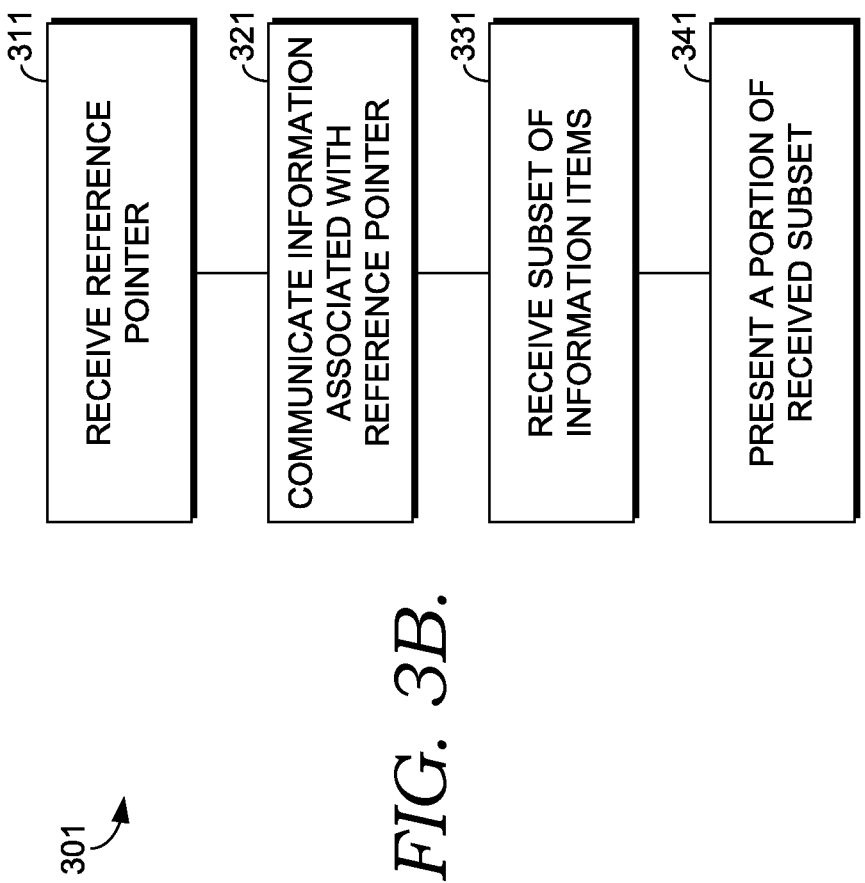

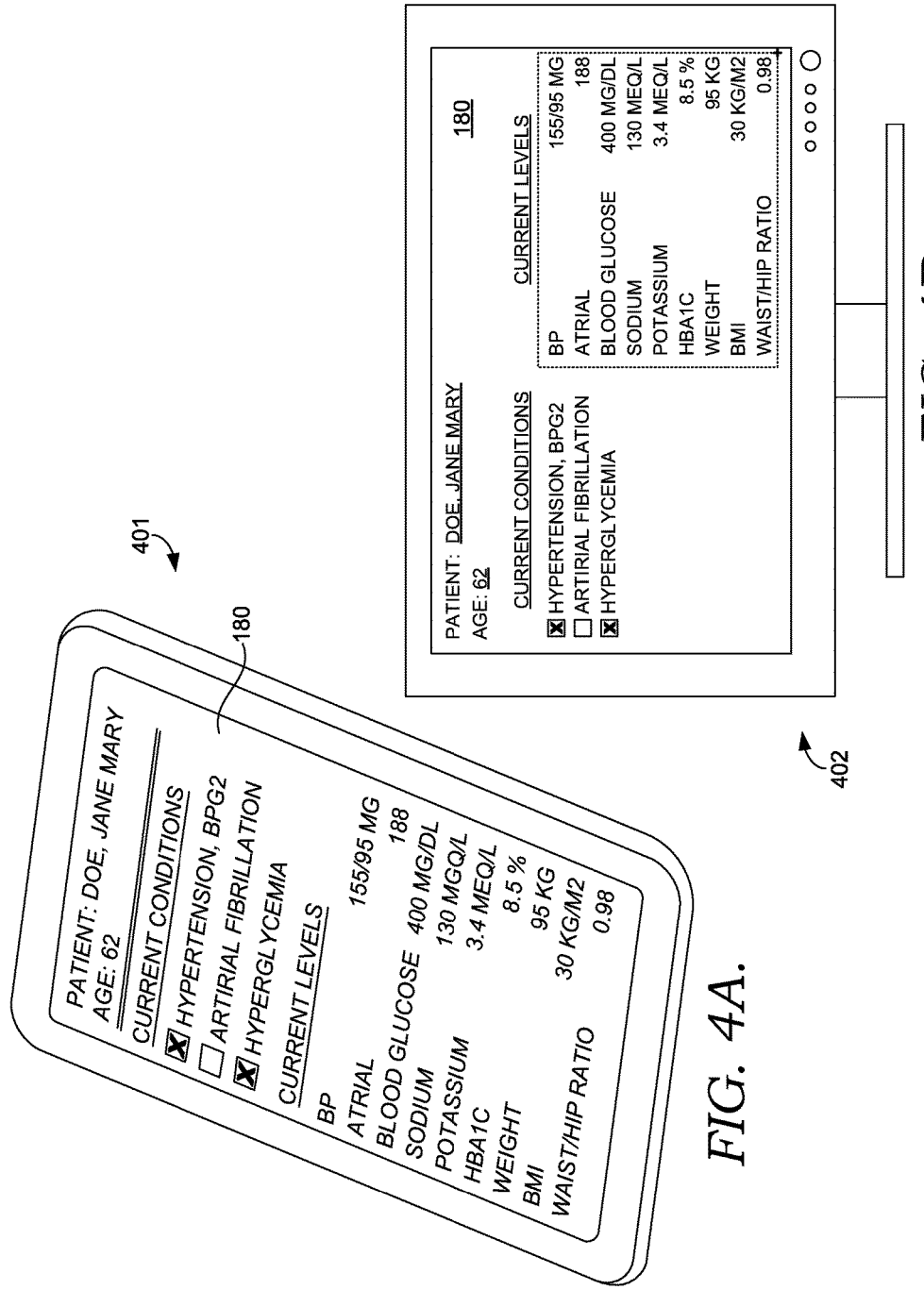

COMPUTERIZED SYSTEMS AND METHODS FOR PROVIDING MOBILE-DEVICE UPDATES OF ELECTRONIC HEALTH RECORDS

CROSS-REFERENCE TO RELATED APPLICATIONS

This application is a continuation of, and claims priority from, U.S. patent application Ser. No. 14/841,093, filed Aug. 31, 2015, entitled "Computerized Systems And Methods For Providing Mobile-Device Updates Of Electronic Health Records," which is a continuation of, and claims priority from, U.S. patent application Ser. No. 13/738,277 (now U.S. Pat. No. 9,141,726), filed Jan. 10, 2013, entitled "Computerized Systems And Methods For Providing Mobile-Device Updates Of Electronic Health Records," which claims the benefit of U.S. Provisional Application No. 61/585,102, titled "Computerized Systems And Methods For Providing Mobile-Device Updates Of Electronic Health Records," filed Jan. 10, 2012; each of which is hereby expressly incorporated by reference in its entirety.

INTRODUCTION

The modern practice of medicine poses a number of information-related challenges for clinicians to effectively deliver quality care to patients. Likewise, information-related challenges arise for patients and their family members, challenges to their effectively tracking and responding to new information that arises at various times during the process of care delivery. In particular, the rate of ongoing arrival of new information about each patient's health continues to grow at a rapid pace, making it difficult for clinicians to keep up with and carry out recognized best practices in a timely, responsive manner. The difficulty for patients or for family member caregivers to keep apprised of new information concerning their own health conditions or those of the family members for whose care they are responsible is exacerbated by the fact that consumers are typically pulled in many different directions by a vast number of daily concerns.

In a similar manner, clinicians have their attention fragmented by heavy patient loads and must often make quick decisions regarding a patient's treatment. The limited time available when new information materializes may be too short to permit the clinician or the consumer to consult the entirety of the individual's electronic health record or personal health record, 'pull' a collection of older context-providing information, and acquaint or reacquaint himself/herself with the context into which the new information fits. As a result, gaps currently exist between recognized best practices and actual clinician decisions; gaps also exist between optimal, fully-deliberated consumer intentions and actual consumer decisions. These gaps contribute to delays, decreased quality of care, increased risk of medical errors, and increased cost of health care.

SUMMARY

Systems, methods, and computer-readable media are provided for facilitating clinical decision making based on a patient's clinical situation by providing up-to-date information, such as patient-related information, to a decision maker. In one embodiment, the method includes the step of receiving a selection of one or more information items associated with a third person. For example, a health-care provider might select a particular topic, concept, or group of interrelated concepts, such as heart-related data, associated with a third-person patient. The method also includes the steps of determining a set of information items related to the one or more selected items. The method also includes the step of associating with the set of information items, a reference pointer, which identifies the set of information items and in some embodiments encoding the reference pointer as a 2-D barcode. The method further includes communicating the reference pointer to a user device, and receiving from the user device a request for information from the set of information identified by the reference pointer. The method further includes the step of providing a subset of information items in the set to the user device. In an embodiment, the subset of information items provided to the user device is based upon a set of criteria that can include, for example, the staleness of the information items and the relevance of the information items to a patient's condition. In an embodiment, the credentials are also received from the user device, which indicate which information items a user, associated with the user device, is permitted to access or how long a portion of the information items should remain accessible to the user device.

BRIEF DESCRIPTION OF THE DRAWINGS

The present invention is described in detail below with reference to the attached drawing figures, wherein:

FIGS. 1A, 1B, 1C, and 1D depict embodiments of the invention and aspects of an illustrative operating environment suitable for practicing embodiments of the invention;

FIGS. 3A and 3B depict flow diagrams of exemplary methods for providing clinical decision support, in accordance with embodiments of the invention;

FIGS. 4A and 4B depict examples of user interfaces suitable for use in embodiments of the invention;

DETAILED DESCRIPTION

Figure 1A:
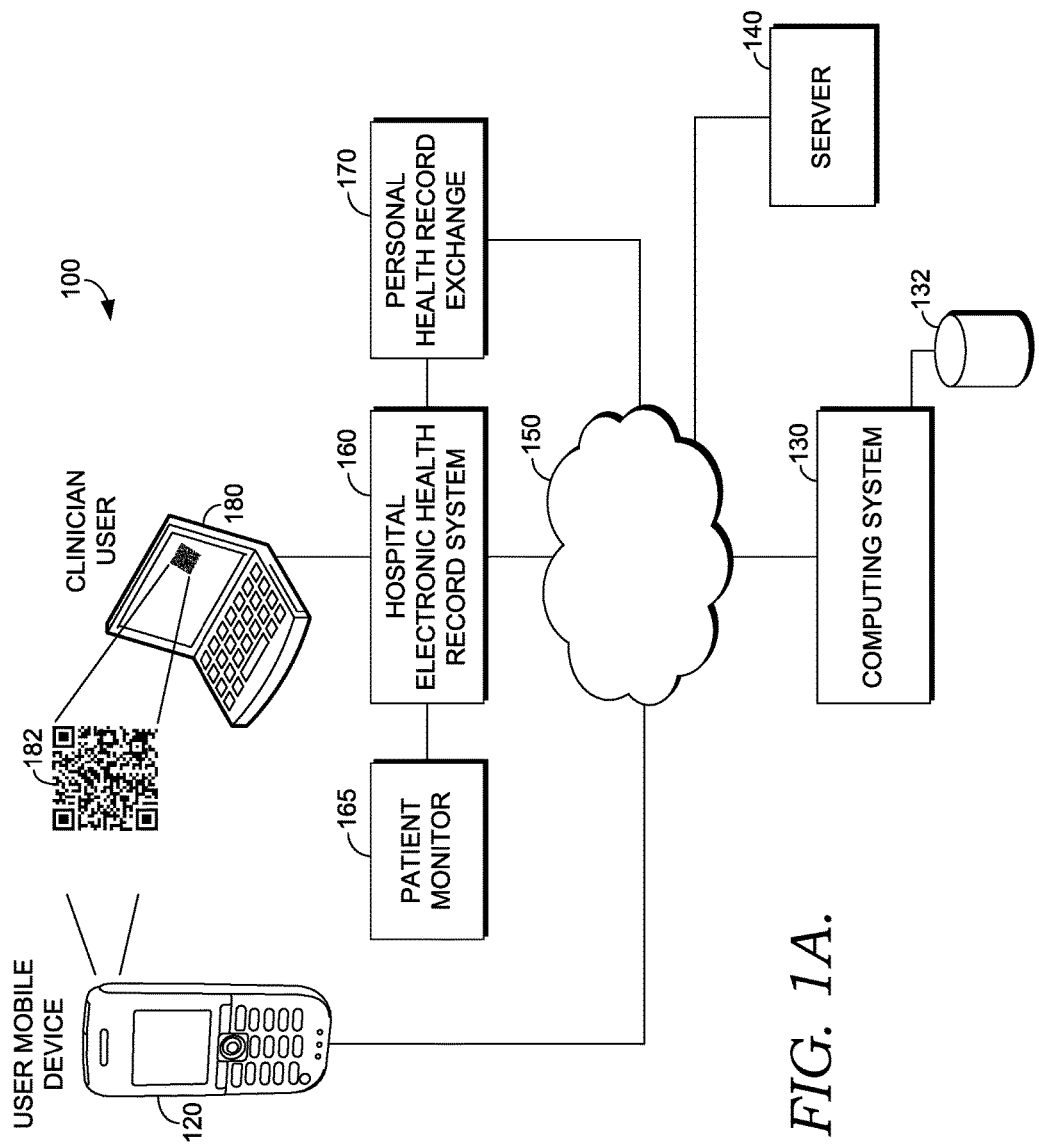

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media.

Computer-readable media include both volatile and nonvolatile media, removable nonremovable media, and contemplate media readable by a database, a switch, and various other network devices. By way of example, and not limitation, computer-readable media comprise media implemented in any method or technology for storing information, including computer-storage media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other storage devices. These technologies can store data momentarily, temporarily, or permanently.

A convenient means to request to receive updated information such as patient-oriented, venue-oriented, or role-oriented topics of ongoing relevance to the clinician requestor or consumer requestor is provided, using for example mobile devices. Tagging and requesting topical, concept-oriented clusters of information so as to cause automatic 'push' or 'pull' delivery of the means to retrieve concise, context-associated information clusters via mobile phones or other media utilized by the requestor can effectively ameliorate cognitive gaps and solve the problems discussed above. The meaning of the new information pertaining to the patient is thus more readily apprehended, and this can in turn promote better, more timely health-care decisions.

Embodiments of the present invention provide a computerized system, methods, and computer-readable media for use in facilitating clinical decision making based on a patient's clinical situation. By way of example and not limitation, a user initiates a request to subscribe to a particular topic, concept, or set of interrelated concepts associated with a third party such as a patient, venue, or role by pointing at one or more active hotspot regions on an electronic health record or personal health record monitor display, or by indicating by a rubber-banding pointing gesture the items of interest on such a display, or otherwise selecting one or more items of interest. A health information system responds by dynamically generating a 2-dimensional barcode associated with the combination of concepts that are associated with the indicated items. The 2-D indicia are presented via the user's monitor display such that the user can take a digital photograph of the 2-D indicia using a camera of a mobile device equipped with application software to decode the barcode and communicate the user's account information with the responding health information system. The user's identity is authenticated by the information system and the user's access privileges are checked.

Continuing with this example, when a clinical decision support event is subsequently triggered (either automatically or manually in various embodiments) regarding concepts to which the user has subscribed, the validity and then-current active status of the subscribed user's access privileges to the information are once again checked, and, if active and valid, the stored clinical information available for that patient and for the tagged-subscribed concepts that are relevant to the clinical decision support event are accessed. A system-generated link or access-means or message containing the relevant topical, concept-associated clusters of information are presented to the clinician user or to a consumer user. In one embodiment, this information is transmitted to the user's mobile device and presented on the mobile device via application software. Alternatively, the information may be contained in SMS text message or other general-purpose application software resident on the mobile device. In yet other embodiments, the information may be contained in an electronic mail message.

Referring to the drawings in general, and initially to FIG. 1A in particular, an exemplary operating environment 100 is provided suitable for practicing an embodiment of our invention. We show certain items in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data stores distributed across multiple locations). But showing every variation of each item might obscure the invention. Thus for readability, we show and reference items in the singular (while fully contemplating, where applicable, the plural).

As shown in FIG. 1A, environment 100 includes computing system 130. In some embodiments, computing system 130 includes an adaptive multi-agent operating system, but it will be appreciated that computing system 130 may also take the form of an adaptive single agent system or a non-agent system. Computing system 130 may be a distributed computing system, a centralized computing system, a single computer such as a desktop or laptop computer or a networked computing system. Some embodiments of computing system 130 include computer software stack, such as software stack 121 of FIG. 1C, which in some embodiments operates in the cloud, as a distributed system on a virtualization layer within computing system 130. Furthermore, some embodiments of software stack 121 include a distributed adaptive agent operating system such as system 129 of FIG. C, which may be implemented as a platform in the cloud, and which is capable of hosting a number of software services, such as services 122-128 described in connection to FIG. 1C. Thus, in some embodiments, computing system 130 takes the form of a distributed adaptive-agent computing system or platform, which may further comprise a multi-agent computing system, as described below.

In some embodiments, computing system 130 is a multi-agent computing system. Multi-agent computing system 130 may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control, which promotes the concept of autonomy. Additional information about the capabilities and functionality of agents and distributed multi-agent operating systems, as they relate to our invention, is provided in U.S. patent application Ser. No. 13/250,072, filed on Sep. 30, 2011, which is herein incorporated by reference in its entirety.

Some embodiments of a distributed adaptive-agent computing system 130 include a distributed adaptive agent operating system 129 of FIG. 1C, with the capability of supporting intelligent information retrieval and filtering out noisy data and utilize heuristics to narrow down a search space to assist in solving complex problems. A distributed adaptive-agent computing system 130 facilitates designing individual agent behaviors and their interactions with other agents and with users. In some embodiments, agents employ software services, such as services 122-128 described in connection to FIG. 1C. While in some embodiments, the software services are embodied as agents or as non-agent software routines. In some embodiments, agents continually monitor events to proactively detect problems and leverage reasoning to react and dynamically alter a plan. In an embodiment, agents can be leveraged to determine concepts related or associated with the user-selected items of interest about a patient, and then prioritize those related items based on criteria such as user preferences, user history information, which can include information compiled from multiple users, staleness of the information item, condition of the third person, information items in the set of information items, the user device, or a significance-value associated with an information item. Thus for example, one or more agents may be used to determine which concepts a user, such as a health-care provider, would want to see for a particular patient, given that patient's condition. To facilitate this, the one or more agents might employ information-set logic services 124 of FIG. 1C, in one embodiment. Accordingly, only those prioritized items, then, would be provided to the user's mobile device, in this embodiment.

System 130 comprises one or more processors operable to receive instructions and process them accordingly, and may be embodied as a single computing device or multiple computing devices communicatively coupled to each other. In one embodiment, processing actions performed by system 130 are distributed among multiple locations such as a local client and one or more remote servers. In one embodiment, system 130 comprises one or more computing devices, such as a server, desktop computer, laptop, or tablet, cloud-computing device or distributed computing architecture, a portable computing device such as a laptop, tablet, ultra-mobile P.C., or a mobile phone.

Turning briefly to FIG. 1D, there is shown one example embodiment of computing system 900 that has software instructions for storage of data and programs in computer-readable media. Computing system 900 is representative of a system architecture that is suitable for computer systems such as computing system 130. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1C is provided as one example of any number of computer architectures, such as computing architectures that support local, distributed, or cloud-based software platforms, and are suitable for supporting computing system 130.

In some embodiments, computing system 900 is a computing system made up of one or more computing devices. In an embodiment, computing system 900 includes an adaptive multi-agent operating system, as described above, but it will be appreciated that computing system 900 may also take the form of an adaptive single agent system or a non-agent system. Computing system 900 may be a distributed computing system, a data processing system, a centralized computing system, a single computer such as a desktop or laptop computer or a networked computing system.

Returning to FIG. 1A, computing system 130 is communicatively coupled to information store 132, described below, and communication network 150. Communication network comprises a network or set of communicatively coupled networks that enable data and computer instructions to be communicated among the systems and devices coupled to the communication network 150. In an embodiment, network 150 includes the Internet, and may also include one or more intranets, which may be public or private. In some embodiments, network 150 comprises a cloud-computing network, which is known in the art as "the cloud" and may also include computing system 130. In an embodiment, network 150 includes a telecommunication network for communicating with a mobile device, such as a mobile phone.

Continuing with the embodiment depicted in FIG. 1A, communication network 150 is communicatively coupled to mobile device 120, server 140, Electronic Health Record Information system (EHRI) 160, and Health Record Exchange, (HRE) 170; each of which is now described. In one embodiment, Mobile device 120 is a mobile phone or tablet device able to receive data for example, SMS text messages, email, instant messages, or other data, and present information, or an indication that information is available, to a user. In one embodiment, mobile device 120 is a smart phone, such as an Apple iPhone®, that includes an application program (not shown), referred to as an "app." The app facilitates receiving the reference pointer, which in one embodiment is a 2-D barcode, and presents information items, such as information about a third-party patient, to the user. In one embodiment, the app also provides user credentials for identification or authentication of the user, to server 140. In one embodiment, mobile device 120, or an app running on mobile device 120, is capable of reading QRCode, SPARQCode, EZCode, or other 2-D barcodes. Further embodiments of the app are discussed below in connection to FIG. 5.

Server 140 receives requests originating from mobile device 120, for information identified by the reference pointer, such as subscribed-to information about a third-party patient, and provides that information, or a portion of that information, to the mobile device. In an embodiment, server 140 communicates with mobile device 120 through a mobile-device network, such as AT&T, Sprint, or Verizon, for example. In one embodiment, server 140 is included in computing system 130, and in one embodiment, server 140 is distributed across two or more of computing system 130, EHRI 160, and a mobile device network. Thus, in some embodiments, server 140 may be distributed into any component that received a request for information from mobile device 120 and provides information to mobile device 120. Likewise, in some embodiments, computing system 130 includes server 140.

EHRI 160 comprises the health-care provider record system or electronic health record information, which in one embodiment includes electronic health records or medical records for a patient, a collection of patients, or a population. HRE 170 comprises a health record exchange.

The embodiment depicted in FIG. 1A further includes a patient-monitor 165 and user interface 180. Monitor 165 determines various physiological levels of a patient, such as for example, cardio and respiratory information. In one embodiment, monitor 165 takes the form of a bedside monitor such as monitor 165 shown in FIGS. 1C and 2B, and such as may be found in a hospital, and that monitors a patient's vital signs. In one embodiment, monitor 165 comprises a sensor or set of sensors worn by the patient.

User interface 180 comprises a user interface for receiving from a user, an indication of a particular topic, concept or group of interrelated concepts for which the user, or another user, desires to receive updated information. For example, in one embodiment, user interface 180 is capable of receiving a selection by a user of items of interest about a third-party patient, for which the user desires to monitor by receiving updates of information related to the selected items of interest on the user's mobile device. In some embodiments, interface 180 takes the form of a touch screen, a display, an electronic clipboard or chart, tablet computer, laptop computer, bedside patient monitor, a mobile device, or any similar device capable of receiving input from a user of items of interest about a patient, topic, or concept, including for example a speech-recognition user interface. User interface 180 may be a single device or a combination of devices, which may be distributed at different locations, and may be stationary or mobile.

Illustrative examples of user interface 180 are depicted in FIGS. 4A and 4B. FIG. 4A depicts an embodiment of user interface 180 in the form of an electronic chart and FIG. 4B shows an embodiment as a display. In one embodiment, the user interface of FIG. 4B includes a touch screen, and in one embodiment, user interface 4B includes other input means such as a keyboard, mouse, pad, voice-recognition module, or other means for receiving, from a user, an indication of information items. For example, in one embodiment, a user "checks" a checkbox adjacent to the information items for which he or she is interested in receiving updated information. In another embodiment, a user draws a box or loop around the information items of interest. In another embodiment, the user otherwise selects or provides an indication of information items of interest.

Returning to FIG. 1A, in some embodiments user interface 180 is capable of displaying to the user a graphic 182 encoded with information associated with the reference pointer. In one embodiment, encoded graphic 182 is a 2-D barcode that contains information associated with the reference pointer that identifies the set of information items related to the information items indicated by the user through user interface 180. In some embodiments, encoded graphic 182 is a 2-D barcode encoded in QRCode, SPARQCode, EZCode, or other 2-D barcoding scheme. In one embodiment, the reference pointer may be communicated to mobile device 120 by first displaying encoded graphic 182 on user interface 180, and then capturing an image of encoded graphic 182 on mobile device 120. Thereafter, an app or other software on mobile device 120 may be used to determine the reference pointer by decoding the image of encoded graphic 182.

As shown in FIG. 1A, environment 100 also includes information store 132. Information store 132 stores information including data and executable code used to facilitate providing mobile-device updates of electronic health records. In some embodiments, this information includes, for example, user subscription information or information otherwise identifying a set of information items related to the information items indicated by the user; user-access permissions or authentication information; mobile-device identification codes; patient health records; health-care provider records; parameters used by a distributed adaptive agent operating system including, for example, criteria for identifying and prioritizing the set of information items related to the information items indicated by a user; rules engine(s) and associated parameters for determining which information to provide to a mobile-device based on the indication received by a user; and user preferences.

Although shown as a single information store, information store 132 may comprise multiple separate dedicated information stores. For example in one embodiment EHRI 160 may have a dedicated information store. In some embodiments, information store 132 comprises networked storage or distributed storage including storage on servers located in the cloud. Thus, it is contemplated that for some embodiments, the information stored in information store 132 is not stored in the same physical location. For example, in one embodiment, one part of information store 132 includes one or more USB thumb drives or similar portable data storage media. Additionally, in some embodiments, data stored in information store 132 can be searched, queried, analyzed using system 130 or user interface 180. In embodiments where information store 132 is distributed, portions of information stored in store 132 may be logically located behind a firewall or otherwise have limited access or require security validation for access.

Figure 1B:
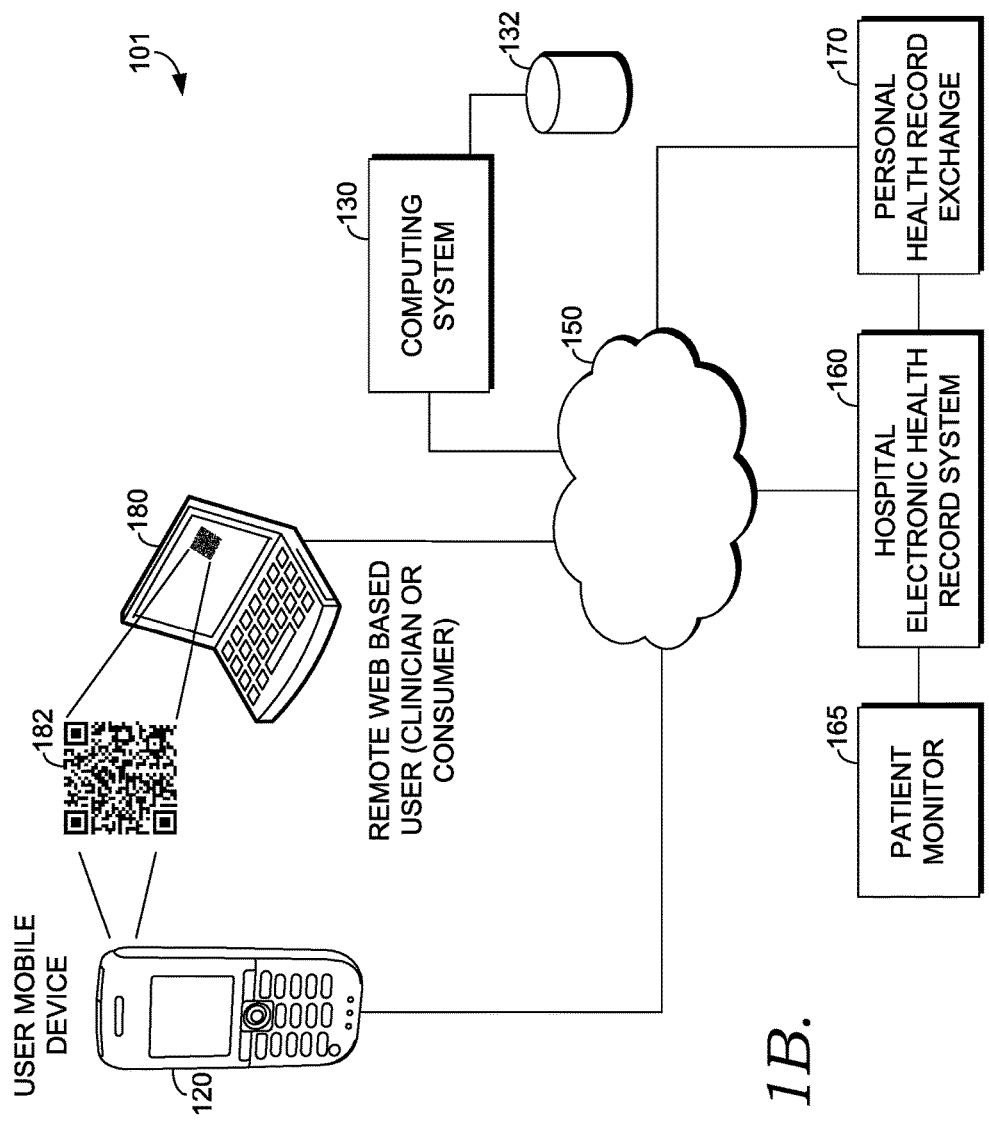

Turning to FIG. 1B, exemplary operating environment 101, suitable for practicing an embodiment of our invention, is provided. Environment 101 includes some of the components of environment 100 described above in connection to FIG. 1A. In environment 101, user interface 180 is depicted as communicatively coupled to EHRI 160 through network 150. In this embodiment, user interface 180 may be more suitable for use by a consumer or clinician. Additionally, server 140 is not shown as embodiments of computing system 130 include server 140.

FIG. 1C is provided as another aspect of an operating environment 102 suitable for practicing embodiments of the invention. In particular, example operating environment 102 depicts software stack 121. As described above in connection to FIG. 1A, embodiments of computing system 130 include computer software stack 121, which in some embodiments operates in the cloud, as a distributed system on a virtualization layer within computing system 130. Some embodiments of software stack 121 include a distributed adaptive agent operating system 129, which may be implemented as a platform in the cloud, and which is capable of hosting a number of services such as 122, 123, 124, 126, 127, and 128. Embodiments of services 122 through 128 run as a local or distributed stack in the cloud, on one or more personal computers and servers such as 130, and/or a computing device such as device 120 or a device supporting user interface 180. In some embodiments, services 122 through 128 take the form of one or more software programs or routines, which may be employed by a software agent, and in some embodiments one or more of services 122 through 128 is embodied as a software agent. Device 120 and the device supporting user interface 180 operate in conjunction with software stack 121, in some embodiments.

Authentication services 122 and access control permissions services provide security and privacy related services for validating transactions with mobile device 120 including subscription requests, such as described in connection to subscription service 190 of FIG. 2A and step 350 of FIG. 3A. For example, in some embodiments services 122 and 124 facilitate validating credentials information. Information-set logic services 124 facilitates determining the set of information items, such as at step 320 of the method described in connection to FIG. 3A, including ranking and prioritizing the items. In some embodiments, services 124 also facilitates determining the subset of information items such as described at step 360 of the method in FIG. 3A. In some embodiments the services 124 operates in conjunction with message assembly services 126 for determining the subset of information items such as described at step 360. Message assembly services 126 facilitates the preparation or receipt of information communicated to or from device 120, such as described in steps 310 and 360 of FIG. 3A and steps 311 and step 311 of FIG. 3B. Update subscription registry service 128 facilitates maintaining the registry of subscriptions such as described in connection to subscription service 190 in FIG. 2A. In some embodiments, subscription registry services are carried out my updates subscription service 190. Some embodiments of software stack 121 include software services 128, which may be embodied as an Apache Hadoop and Hbase framework, or similar frameworks operable for providing a distributed file system.

Figure 2A:
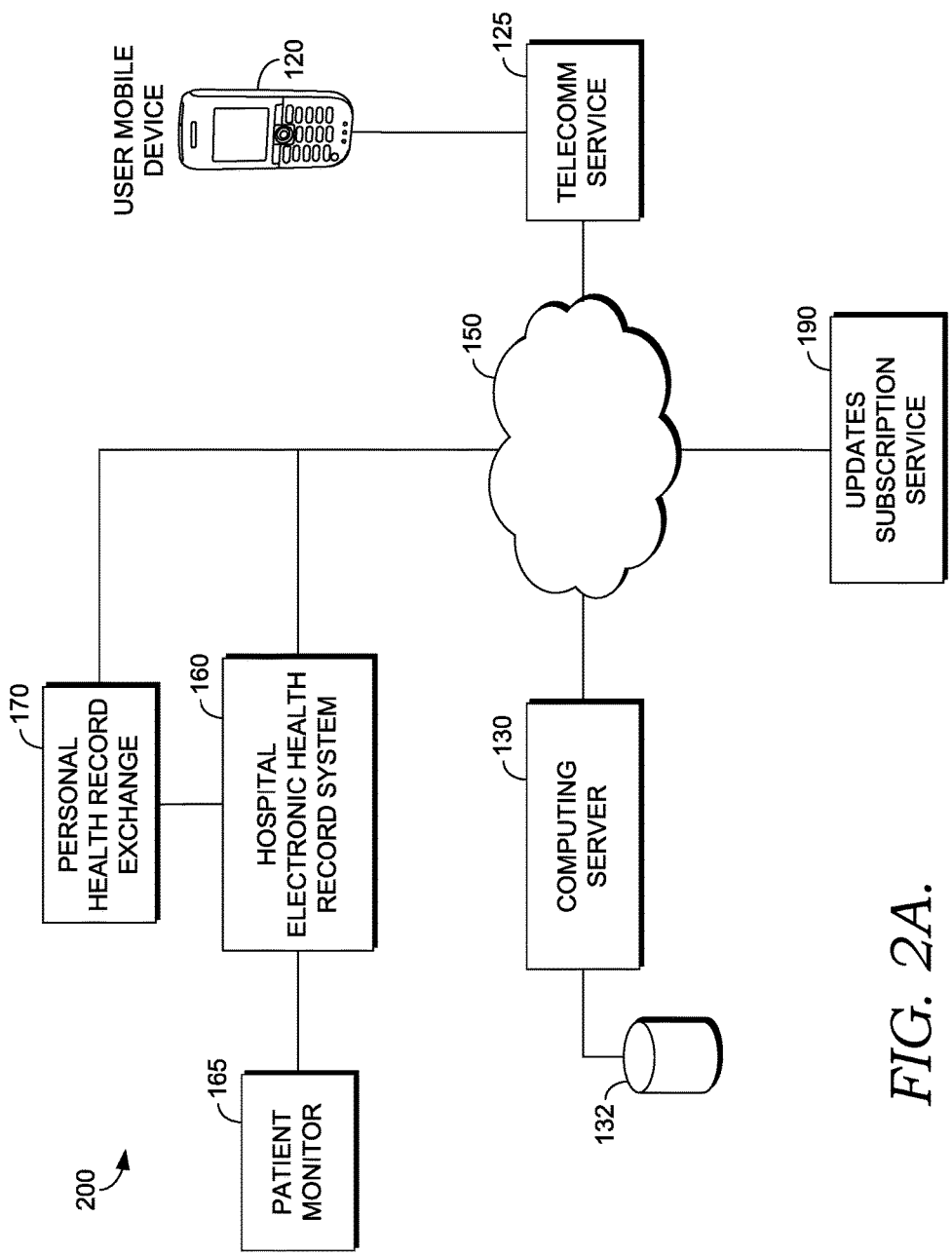
FIGS. 2A and 2B depict embodiments of the invention and aspects of an illustrative operating environment suitable for practicing embodiments of the invention also showing telecom or mobile data services.

FIG. 2A depicts another exemplary operating environment 200 suitable for practicing an embodiment of our invention. In environment 200, mobile device 120 is communicatively coupled to telecom service 125. In some embodiments, telecom service 125 is provided by a mobile service provider such as AT&T, Sprint, or Verizon, for example, and includes mobile web or data service, mobile e-mail service, mobile SMS service, or a combination of these services. Environment 200 also includes updates subscription service 190. Subscription service 190 facilitates user-subscription functionality and in some embodiments includes an update subscription registry, which includes information specifying subscriptions and registers information updates for subscribed-to concepts, topics, groups of concepts, or information items. In one embodiment, the update subscription registry is used to determine which updates a user's mobile device should receive, based, in one embodiment, on information about available updates and, in one embodiment, also based on information about which updates the mobile device has already received. In one embodiment, subscription service 190 receives information from mobile device 120 specifying information about the user's mobile device, bandwidth, data connection speed, user feedback, and other information in addition to information related to the reference pointer. Subscription service 190 uses this additional information for managing the communication of a subset of information items, from the set of information items identified by the reference pointer, to the mobile device, in one embodiment. For example, subscription service 190 may throttle the information or only provide the most important information items, where a mobile device's data connection is limited. In one embodiment, the communication is managed by computing system 130 or server 140, and in one embodiment, the information received from mobile device 120 is used to determine the priority or ranking of the information items in the set of information items, as further described below in connection to step 320 of FIG. 3A.

In some embodiments subscription service 190 receives a subset of information items related to those items subscripted to (or indicated by) a user, and facilitates the communication of the subset of information items to the mobile device. For example, subscription service 190 may prepare for sending via SMS, a message containing a secure hyperlink to the subset of information items, in an embodiment. In an embodiment, subscription service 190 functions as a server, such as server 140, and in one embodiment, subscription service 190 is part of server 140 or part of computing system 130. For example, in an embodiment subscription service 190 takes the form of one or more software programs or routines, or software agents residing on computing system 130.

In one embodiment, subscription service 190 receives requests from a mobile device for information associated with the reference pointer. In one embodiment, subscription service 190 manages the security and authentication of a user's mobile device when a request is received or before third-party information is provided to the mobile device. In some embodiments, subscriptions may expire. For example, a user may only be permitted to view data about a particular patient for a limited duration of time. Or after a period of time, information about a particular patient may no longer be useful (e.g., if the patient has recovered and is no longer being monitored.) It is contemplated that in such embodiments, subscription service 190 manages the subscription lifetimes, thereby facilitating individual subscriptions to expire or be renewed. In one embodiment, subscription service 190 throttles information provided to mobile device 120. In one embodiment, the throttling is intelligently determined using a rules engine or agent, such that only the most important information is updated as it becomes available, and less important information items are updated periodically, such as once every hour. In one embodiment, subscription service 190 throttle information so as to conserve bandwidth usage.

Figure 2B:
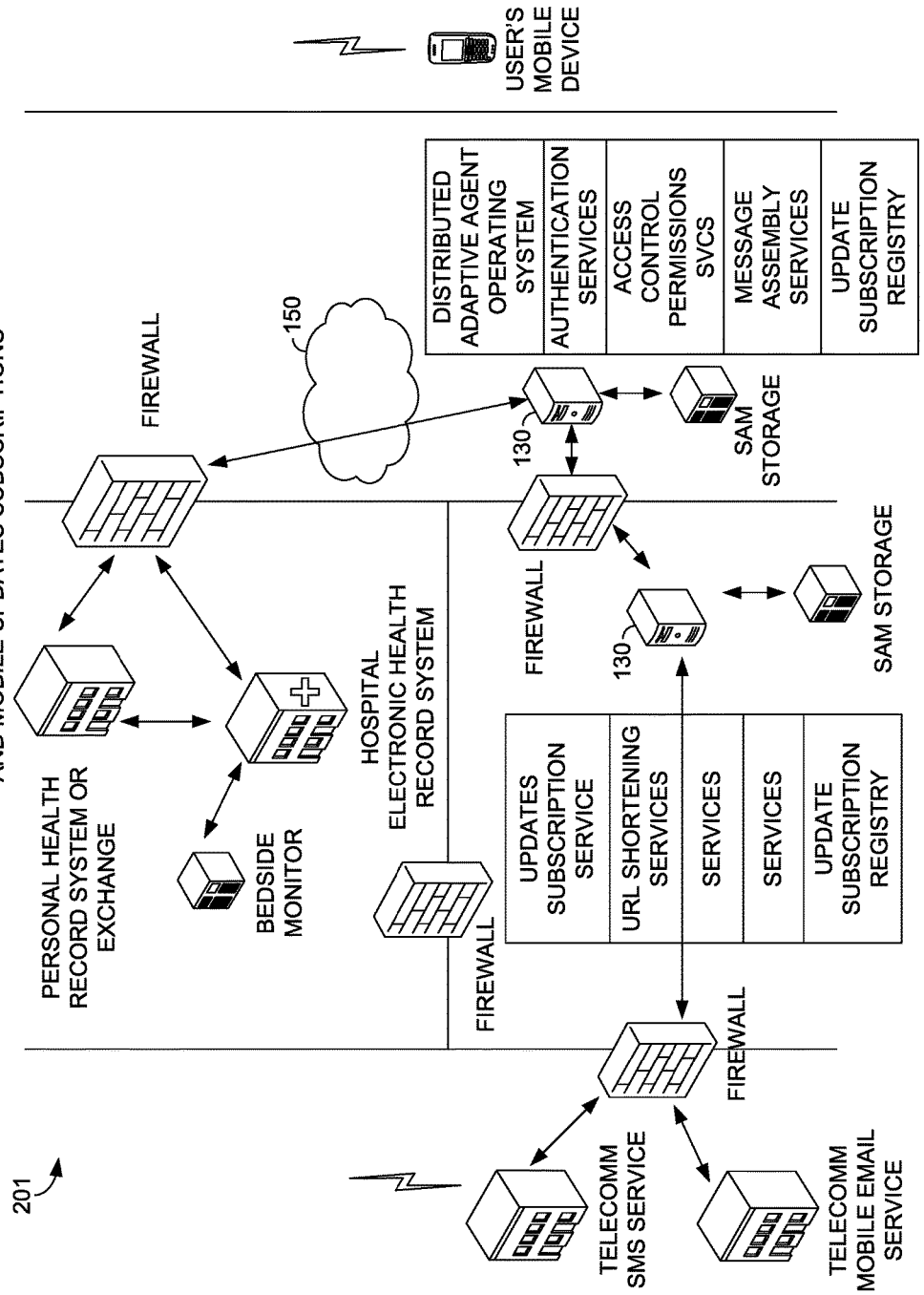

FIG. 2B is provided as an example of other operating environments suitable for practicing embodiments of the invention and includes many of the same components described in connection to FIGS. 1A-1D and 2A.

Figure 3A:
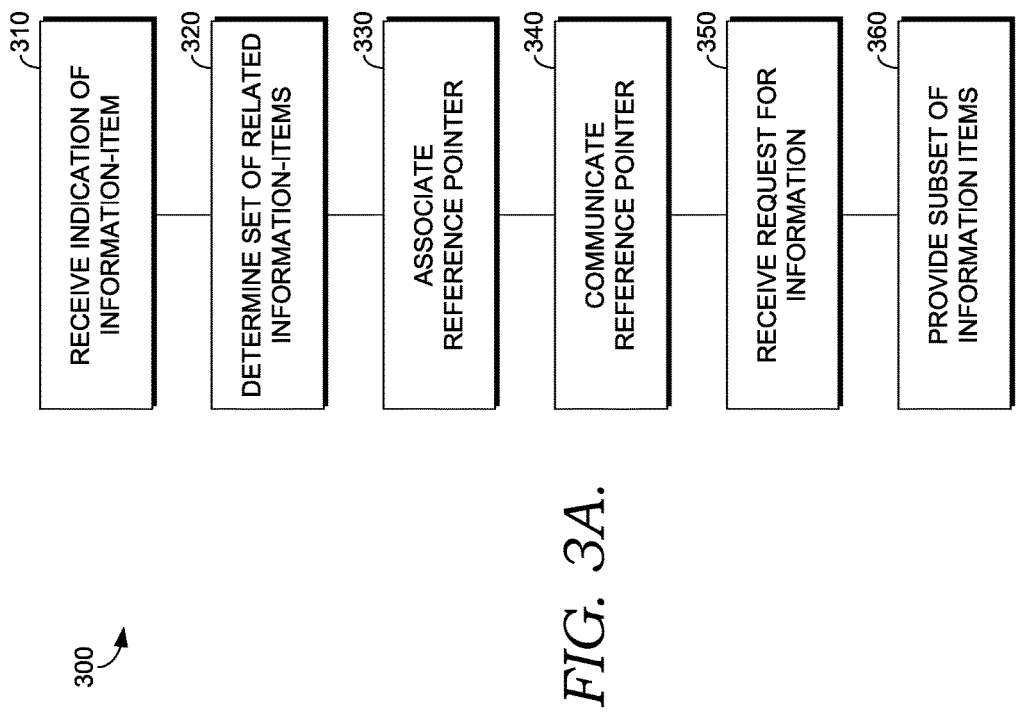

Turning now to FIG. 3A, a flow diagram 300 is provided illustrating, at a high level, an exemplary method according to one embodiment. At a step 310 an indication of one or more information items is received. The one or more information items may be received by way of user interface 180, mobile device 120, or a communication such as a request, received by mobile device 120 or computing system 130. In one embodiment, the information items include topics, concepts, or group of interrelated concepts associated with a third person, such as a patient. By way of example and not limitation, in one embodiment, while browsing in Electronic Health Records (EHR) or Patient Health Records (PHR), a clinician user or consumer user notices an information item of interest. Here, the information items might include, for example, patient-related item(s), about which the user wishes to receive automatic future updates; venue-related item(s), such having an Mpage for a particular unit delivered to the user until the user is no longer on-call; or role-related item(s), such as all cardiology consults until the user is off-service. In one embodiment, information items are associated with one or more index codes, such as the Cerner Knowledge Index (CKI), which identify or categorize information items as structured discrete data elements that can be represented by coded concepts within a data dictionary or an ontology. In one embodiment, a health-care provider selects information items associated with a patient, and the items are received through a user interface, such as user interface 180. For example, turning briefly to FIGS. 4A and 4B, a health-care provider might select (as indicated by the checked checkboxes) the Hypertension and Hyperglycemia information items. These selected items are then received via user interface 180. In one embodiment, an indication of one or more information items is received via a user interface 180 as a selection of items, from a user. In one embodiment, the user rubber-bands or groups a set of information items on the user interface 180, and then clicks a button or touches the screen to indicate that he or she wishes to subscribe to information related to that group of information items. In one embodiment, an indication of one or more information items is provided by an agent or recommendation engine, which may take the form of a request. In this embodiment, the indication might not be received by user interface 180, but instead received directly by computing system 130 or server 140.

In some embodiments, an indication of one or more information items is received through mobile device 120 by way of audio or visual information. For example, using mobile device 120 a user may speak a request for information items directed to mobile device. The mobile device then employs voice-recognition functionality to decode the words spoken in the user's request. In embodiments, the decoded words are then analyzed to determine the one or more information items. In another example, using a camera feature of mobile device 120, a user may capture an image which contains graphical information of the items of interest, such as a picture of a patient's chart. In some embodiments, the mobile device 120 may then employ object-character-recognition or patter recognition functionality to determine the information items from the captured image. While in some embodiments information representing the captured image is communicated to computing system 130 where character or pattern recognition is performed to determine information items. Additionally, in the example of receiving audio of visual information, some embodiments may employs a confirmation step allowing the user to confirm the information items before continuing.

At a step 320, a set of information items is determined such that members of the set of items are related to the information item for which an indication was received at step 310. For example, if the indication of an information item received in step 310 was for hypertension, then at step 320, a set of information items related to hypertension is determined; this set might include blood pressure, sodium levels, weight, and other information items related to hypertension. In one embodiment, information-set logic services 124 is used to determine the set of related items. Logic services 124 may further employ rule tables, a rules engine, or software agents. Thus in one embodiment, one or more agents determine the set of related information items; for example an agent may learn that a particular information item has significance for a patient with a given condition, and thus include that information item in the set of information items. In embodiments using index codes, such as CKIs, the CKIs corresponding to the indicated information items are first determined. Then, a set of information items is determined based on those CKIs.

In one embodiment, the set of related items is prioritized or is ranked according to criteria, such that a subset of information items, based on rank or priority, can be determined and communicated to a mobile device. In particular, in some situations, it is impractical to provide to the mobile device every information item in the set of information items. Not only is a smaller display screen on a mobile device less auditable for viewing large amounts of information, even if it were, the user may not want to sift through that much information. Some information items are less significant or meaningful or outdated, while other information items may be more relevant to determining a patient's condition. For example, if the third party is a patient who recently suffered a heart attack, then information items for blood-pressure and pulse carry more significance for this patient than if the patient were a teenager with a broken arm; accordingly blood pressure and pulse would likely be determined to have a higher priority for this patient, than if the patient were a teenager. Thus in some embodiments, it is desirable to rank or prioritize the information items, so as to maximize value to the user.

In some embodiments one or more criteria are used to perform the prioritization or ranking of the information items. Furthermore, in some embodiments, the ranking or prioritization may be determined by an agent, logic or rules engine, or by user preferences. For example, in one embodiment, a user or agent may designate a particular information item or class of information items as being more important. For example, if the user is a health-care provider who is monitoring only patients who are pregnant, the user may always prefer to see the blood pressure (or the class of information items concerning blood, which could include blood pressure, pulse, various chemical-levels present in the blood, and other blood-related information items). In one embodiment, historical information, such as previous user actions, preferences, and user patterns—from a single user or multiple users—may be used as criteria for prioritization or ranking. For example, if users repeatedly associate a given information item with a patient having a certain condition, then over time, that item may be weighted as having a higher priority for patients with a similar or identical condition.

In one embodiment, the criteria include the age or staleness of a particular information item. For example, a user would be less interested in receiving an update of an information item that has not changed or is no longer relevant. (E.g., a user would probably not be interested in receiving updated information about a patient's pulse from three weeks ago.) Individual information items and classes of information items may have a temporal value associated with them, in some embodiments, which can indicate for how long the information is considered useful. In one embodiment, an agent or rules engine, using a rules table for example, determines the useful lifetime of a particular information item based on that item and the patient's condition. For example, a table may indicate that an information item for pulse when the third party patient is a teenager is only significant for 2-3 hours. Thus, this information item would have a higher priority (or better ranking) within the first 2-3 hours after the pulse was determined. Afterwards, its priority or ranking would diminish. Accordingly, as time passed beyond 2-3 hours, it would be increasingly less likely that the pulse information item would be communicated to the mobile device because its priority (or ranking) would be lower. This is different from the temporal aspect of the user's subscription, discussed below, which contemplates that a user may only desire to know about or be permitted to access information about a third-party patient for a given amount of time or that a user's access may be temporary. In these cases, the user's subscription to a set of information items may expire after a period of time.

In some embodiments, the criteria include a third party's condition. For example, where the third party is a patient who just suffered a heart attack, information items related to the heart might be determined to have a higher priority (better ranking) than those information items would have, if the patient were a teenager with a broken arm. In some embodiments, the criteria include information about the group of items that the user selected or were indicated in step 310. In some embodiments, the criteria include information about the number of third parties that a user is subscribed to or is receiving updates for. In these embodiments, which are described below in connection to step 360, care is taken not to flood the user with excess information, thereby diminishing the value of providing the user with updated information on a mobile device. In one embodiment, the criteria include the significance of change in a particular information item or group of information items. For example, a minor change in heart rate of 3 to 4 beats per minute is less significant than a major drop in blood glucose levels. Thus, an updated information item that indicates a change in heart rate of +3 beats per minute would have a lower priority (worse ranking), than an updated information item indicating a major change in blood glucose levels of +200 MG/DL.

Continuing with FIG. 3A, at a step 330, a reference pointer is associated with the set of related information items. In an embodiment, the reference pointer is an address, such as a URL, physical address, logical address, or mapping to a location in information store 132 that stores the set of related information items. In an embodiment, the reference pointer comprises information usable by computing system 130 to determine the one or more information items provided by in step 310. In an embodiment, a reference pointer is a set of pointers or addresses to all of the individual pieces of information items in the set. In an embodiment, a reference pointer is a code that is associated with an identifier, such as a physical address, or logical address, or table of addresses, that identify the set of related information items. For example, in this embodiment, a table or database may be associated with the reference pointer (here a code), thereby mapping the reference pointer to the set of information items. One advantage of having a reference pointer as a code and not an actual physical or logical address is that the code can always be the same length. Additionally, the code might be rendered meaningless without the associated identifier; thus, security advantages are provided because the reference-pointer code can be communicated without identifying any information about the set of information items that are associated with the reference pointer. Thus, for example in one embodiment a pseudorandom code can be generated, using computing system 130, and used as reference pointer by associating it with a set of information items. Moreover, the association between the code and the set of information items is made secure so that only a user with authorized credentials can access information in the set of information items. An unauthorized user might not be permitted to see or detect the association, let alone the set of information items.

At a step 340, the reference pointer is communicated to a mobile device. In one embodiment, the reference pointer is sent via SMS text message or e-mail to the mobile device. In one embodiment, the reference pointer is communicated over Bluetooth, Wi-Fi, or other wireless-communication technologies. In one embodiment, the reference pointer is communicated to the mobile device as an update within an app. For example, an app running on the mobile device might include functionality for receiving the reference pointer. In one embodiment, the reference pointer is encoded within a graphical image, such as a 2-D barcode, and communicated to the mobile device by way of capturing the image using the mobile device. For example, computing system 130 might encode the reference pointer as a 2-D barcode, which can be presented on user interface 180, in one embodiment. Using a camera on mobile device 120, a user can capture an image of the 2-D barcode. Subsequently to capturing the image, an app on mobile device 120 can be used to decode the reference pointer from the 2-D barcode image. In one embodiment, an image of the 2-D barcode (or graphic image) is not captured on the mobile device, but rather an app, running on the mobile device and using the camera, reads and decodes the reference pointer from the image.

At a step 350, a request is received for information from the set of information associated with the reference pointer. In one embodiment, mobile device 120, having received the reference pointer, now requests information pointed to by the reference pointer. The request is received by server 140, subscription service 190, or a server operating on computing system 130, in an embodiment. For example, in one embodiment, if a user has subscribed to heart-related information about a particular patient, the user's mobile device 120 (having received the reference pointer, which points to information from the set of heart-related information determined in step 320) now communicates a request for information that is associated with the reference pointer. In one embodiment, mobile device 120 communicates the reference pointer, or information associated with the reference pointer such as a portion of the reference pointer code, to server 140 or subscription service 190.

In one embodiment, mobile device 120 may also communicate credentials or authorization information. In some embodiments, credentials or authorization information includes user credentials, subscription credentials, or both. In one embodiment, user credentials identify the user, which can be used to determine which information or which types of information a user is permitted to access. In one embodiment, user credentials do not identify the user, but specify the information or types of information that a user is permitted to access. Subscription credentials specify information about the user's subscription, which in one embodiment, can be discretized to a per-patient or per-information item level. In one embodiment, subscription credentials include authorization information from the third party for which the information is concerning. In one embodiment, subscription credentials specify how long a particular information item or set or subset of information items, can be accessed. For example, if a user is authorized to access data for a patient only for a specified period of time, then after the credential expires, the user will no longer be permitted to access updated information for that patient. In one embodiment, a user may only desire to know about a third-party patient for a given amount of time. In the proceeding embodiments, the user's subscription to a set of information items or a particular information item may expire after a period of time. In one embodiment, the mobile device will no longer request information after the subscription has expired. In one embodiment, the mobile device will display an indication to the user that the user's credential has expired or that the user is not permitted to access the information requested.

In one embodiment, the health-care provider can revoke or grant credentials at any time. For example, in one embodiment, the health-care provider maintains a database, which takes the form of a relational database of credential information associated with users, patients, or concepts. Using this database, the health-care provider can alter credentials associated with a patient, user, or concept, at any time. Thus, the information that a user is permitted to access can be controlled dynamically by the health-care provider. By way of example, if the health-care provider determined that a particular user is no longer permitted to have access to information about a particular patient, then the credential information in the database that is associated with that user and that patient would be set so as to prevent access to the patient information, thereby effectively revoking credentials, in one embodiment.

In one embodiment, a third party, such as a patient, is permitted to provide input for determining credentials. For example, a patient might set access-permission levels; in one embodiment, the patient might do this by logging on to a secure website maintained by the health-care provider. In one embodiment, the third party may identify particular information items for which they desire to block access. In one embodiment, the third party might consent, or provide permission, to allowing information items to be made accessible to a user, such as their doctor, using the technologies of the present invention. In one embodiment, the third party provides the consent by logging on to the secure website. In embodiments such as these, the third party is provided control over what information is made accessible, to whom it is accessible, and for how long it is accessible.

In one embodiment, each subscription or requested information item has a subscription ID or information item ID that is also received at step 350. In one embodiment, the ID includes information about the time that the last update for that subscription or information item was received. Alternatively, the received request can include information specifying when a particular update was last received. In these embodiments, server 140, subscription service 190, or other software services, routines, or agents operating on computing system 130 may determine the time duration since the last update was received and/or which update was last provided to the mobile device. Accordingly, by receiving information about which updates or subscriptions are on the mobile device, server 140 or subscription service 190 can determine which updated information should be provided to the user. Moreover, in some embodiments, the received information about which updates or subscriptions are on the mobile device is used as criteria for prioritizing (or ranking) information items to be provided to the mobile device. For example, suppose that subscription service 190 received information indicating that the last blood-pressure-related information on a mobile device is from over 48 hours ago, then this information may be used to assign a higher priority (or better ranking) to blood-pressure-related information, thereby increasing the likelihood that blood-pressure-related information will be provided in the next update of information sent to the mobile device.

In one embodiment, the received request for information of step 350 may be accompanied by other information, such as for example, information about the mobile device sending the request, the mobile service provider (e.g., AT&T, Verizon, or Sprint), the mobile device's signal strength, or the number of subscriptions to which the user is subscribed. In these embodiments, this information may be used as criteria for prioritizing the set of related information items, or may be used to control which information items are communicated to the mobile device, as described next in step 360, and when those information items are communicated to the mobile device. For example, in situations where the mobile device has diminished signal strength, is roaming, or has a smaller-bandwidth connection such as a 3G connection, it may be advantageous, in some embodiments, to provide fewer information items to the mobile device, or throttle the communication of information items to the mobile device. Thus, only higher priority or ranked information items, or information items determined to be critical or urgent, would be communicated to the mobile device, in these embodiments.

At a step 360, a subset of information items from the set of information items is provided to the mobile device. In one embodiment, the subset of information items includes the higher priority or ranked information items. Thus for example, where the set of information items determined in step 320 includes hundreds of items, which have been prioritized or ranked, at step 360 a subset of this set, comprising the items having a higher rank or priority, is provided to the mobile device, in this embodiment. In some embodiments, the subset of information items is provided using either "push" or "pull" technologies. For example, in one embodiment, the subset is provided as a "push" of information by way of a data connection. In another embodiment, the mobile device "pulls" the subset of information items. In one embodiment, the mobile device receives a notification that updated information is available, and an app running on the mobile device initiates a communication session to receive the subset of information items.

In one embodiment, the determination of which information items are included in the subset is determined by criteria such as the criteria used to rank or prioritize the user preferences. For example, in one embodiment, only urgent or the most highly ranked information items are provided to the mobile device as they become available. Other information items (i.e., those not having high priority) are provided periodically, such as once every several hours. In some embodiments, the communication of subset of information items to the mobile device is throttled. In one embodiment, certain information items may not be provided at all, based on the criteria. For example, suppose a user has subscribed to blood-related information about a particular third party. Thus, in step 310, an indication of blood-related information items were received, and at step 320, the set of all information items related to blood for that patient was determined. Suppose that one blood-related information item in the set is information specifying that the patient's blood type is A+. This information may have little value to a user who is using her mobile device to conveniently monitor a patient's status using the technologies of our invention. (In some embodiments, a software agent or rules engine might determine that blood-type is of little relevance given the patient's condition or historical user information. In some embodiments, the user may have indicated, through a user-preferences setting, that the user doesn't want to see blood-type information.) Thus the patient's blood type will likely be determined to have a lower priority, in embodiments that prioritize the information items. Accordingly, it is possible that the information item about a patient's blood type is not provided to the mobile device as part of the subset provided in step 360.

In some embodiments, the criteria include information about the number of third parties that a user is subscribed to or receiving updates for. In these embodiments, care is taken not to flood the user with excess information, thereby diminishing the value of providing the user with updated information on a mobile device. Thus for a user who is receiving information related to multiple patients, only the most important information for each patient may be provided; but where a user has only one patient, then more information items may be provided.

It is further contemplated that in some embodiments communication of information is done securely so as to minimize the possibility of information theft and comply with HIPPA requirements.

In some embodiments, before or after the subset of information items is provided, a user is able to request additional information about a patient, using his or her mobile device. For example, in some embodiments, an app running on the mobile device may present to the user a button or option to "show more" information about the third party that the user is monitoring. In some embodiments, the user is provided a means to provide feedback based on the subset of information items received. For example, in one embodiment, the user can place orders or add comments or notes into the mobile device, via an app running on the mobile device. Such feedback may be securely communicated to server 140, in one embodiment.

In some embodiments, a confirmation that the subset of information was delivered to the mobile device, occurs. For example, in one embodiment, mobile device 120 sends an indication of receipt of the subset of information to subscription service 190 or server 140. In one embodiment, this receipt is further used to determine which updates to provide to a particular user's mobile device, based on which updates have already been received, and in one embodiment the receipt is used as criteria for ranking or prioritizing the information items in the set of information items. For example, if a mobile device was unable to receive updates for a period of time, such as 18 hours, then a particular information item, such as a patient's pulse from 17 hours ago, may no longer be included in the subset of information items communicated to the mobile device because it is less significant or useful to the user (i.e., it has dropped in ranking or priority). Whereas, if that particular information item would have been included for an update received 16 hours ago, it would no longer be included in the next update communicated to the mobile device.

FIG. 3B depicts a flow diagram illustrating, at a high level, an exemplary method according to one embodiment and is shown as 301. At a step 311 a reference pointer is received by a mobile device. In one embodiment, the reference pointer is an address, such as a URL, physical address, logical address, or mapping to a location in information store 132 that stores a set of information items related to information items, which may also include topics, concepts, or groups of concepts, that a user or agent has selected or indicated. In one embodiment, a reference pointer is a set of pointers or addresses to all of the individual pieces of information items in the set. In one embodiment, a reference pointer is a code that is associated with an identifier, such as a physical address, or logical address, or table of addresses that identify the set of related information items. Further embodiments of a reference pointer are discussed above in connection to step 330 of FIG. 3A.

In one embodiment, the reference pointer is received mobile device 120 at step 311 via SMS text message or e-mail to mobile device 120. In one embodiment, the reference pointer is communicated over Bluetooth, Wi-Fi, or other wireless-communication technologies. In one embodiment, the reference pointer is communicated to mobile device 120 as an update within an app. For example, an app running on mobile device 120 might include functionality for receiving the reference pointer. In one embodiment, the reference pointer is encoded within a graphical image, such as a 2-D barcode, and communicated to mobile device 120 by way of capturing a representation of the image using mobile device 120. For example, computing system 130 might encode the reference pointer as a 2-D barcode, which can be presented on user interface 180, in one embodiment. Using a camera on mobile device 120, a user can capture an image of the 2-D barcode. Subsequently to capturing the image, an app on mobile device 120 can be used to decode the reference pointer from the 2-D barcode image. In one embodiment, an image of the 2-D barcode (or graphic image) is not captured on the mobile device, but rather an app, running on the mobile device and using the camera, reads and decodes the reference pointer from the image.

At a step 321, information associated with the reference pointer is communicated to server 140, subscription service 190, or a server operating on computing system 130. In one embodiment, the communicated information includes a request for receiving information from the set of information associated with the reference pointer. In one embodiment, the mobile device, having received the reference pointer, now requests information pointed to by the reference pointer. The request is received by server 140, subscription service 190, or by a server operating on computing system 130, in an embodiment. For example, in one embodiment, if a user has subscribed to heart-related information about a particular patient, the user's mobile device (having received the reference pointer in step 311), communicates a request for information that is associated with the reference pointer. In one embodiment, the mobile device communicates the reference pointer, or information associated with the reference pointer such as a portion of the reference pointer code, to server 140 or subscription service 190.

In one embodiment, the mobile device may also communicate credential information. In some embodiments, credential information includes user credentials, subscription credentials, or both. The embodiments of using credential information described above in connection to step 350 of FIG. 3A, are also applicable to embodiments of step 321.

In an embodiment, the information communicated in step 321 includes a subscription ID or information item ID. In one embodiment the ID includes information about the time that the last update for that subscription or information item was received by the mobile device. Alternatively, the information communicated in step 321 can include information specifying when a particular update was last received. In these embodiments, server 140, subscription service 190, or computing system 130 is capable of determining how long it has been since the last update was received and/or which update was last provided to the mobile device. Accordingly, by receiving information about which updates or subscriptions are on the mobile device, server 140 or subscription service 190 can determine which updated information should be provided to the mobile device. Moreover, in some embodiments, the received information about which updates or subscriptions are on the mobile device is used as criteria for prioritizing (or ranking) information items to be provided to the mobile device. For example, suppose that subscription service received information indicating that the last blood-pressure-related information on a mobile device is from over 48 hours ago, then this information may be used to assign a higher priority (or better ranking) to blood-pressure-related information, thereby increasing the likelihood that blood-pressure related information will be provided in the next update of information sent to the mobile device.

In one embodiment, the information communicated in step 321 may be accompanied by other information, such as for example, information about the mobile device sending the request, the mobile service provider (e.g., AT&T, Verizon, or Sprint), the mobile device's signal strength, or the number of subscriptions to which the user is subscribed. In these embodiments, this information may be used as criteria for prioritizing the set of related information items, or may be used to control which information items are communicated to the mobile device, and when those information items are communicated to the mobile device. For example, in situations where the mobile device has diminished signal strength, is roaming, or has a smaller-bandwidth connection such as a 3G connection, it may be advantageous, in some embodiments, to provide fewer information items to the mobile device, or throttle the communication of information items to the mobile device. Thus, only higher priority or ranked information items, or information items determined to be critical or urgent, would be communicated to the mobile device, in these embodiments.

At a step 331, a subset of information items from the set of information items associated with the reference pointer, is received by mobile device 120. In one embodiment, the subset of information items includes the higher priority or ranked information items. Thus, for example, where a set of information items, which may be determined as described above in step 320 of FIG. 3A, includes hundreds of items, which have been prioritized or ranked, at step 331 a subset of this set, comprising the items having a higher rank or priority, are received by the mobile device, in one embodiment. In some embodiments, the subset of information items is received using either "push" or "pull" technologies. For example, in one embodiment, the subset of information is "pushed" to mobile device 120 via telecom service 125, server 140 or subscription service 190. In another embodiment, the mobile device "pulls" the subset of information items from server 140 or subscription service 190. In one embodiment, mobile device 120 receives a notification that updated information is available, and an app running on mobile device 120 initiates a communication session to receive the subset of information items.

In one embodiment, a determination of which information items are to be included in the subset is determined by criteria such as the criteria used to rank or prioritize the user preferences. For example, in one embodiment, only urgent or the most highly ranked information items are provided to (and subsequently received by) the mobile device as they become available. Other information items (i.e., those not having high priority) are provided periodically, such as once every several hours. In some embodiments, communication of the subset of information items to the mobile device is throttled. In one embodiment, certain information items may not be provided at all, based on the criteria, as described in connection to step 360 of FIG. 3A.

In some embodiments, the criteria include information about the number of third parties that a user is subscribed to or is receiving updates for. In these embodiments, care is taken not to flood the user with excess information, thereby diminishing the value of providing the user with updated information on a mobile device. Thus, for example, a user who is receiving subsets of information for multiple third-party patients, only the most important information for each patient may be provided; but where a user has only one patient, then more information items may be provided, and subsequently received at step 331.

At a step 341, a portion of the received information is presented on the mobile device. An illustrative example of presenting a portion of a received subset is provided in FIG. 5, which shows information about a third-party patient. In one embodiment, only a portion of the received subset of information is presented because the mobile device 120 may have limited screen size, or a user may only care to see a portion of the information at a time. In some embodiments, the user can scroll, browse, or search through the remaining information in the received subset of information. In one embodiment, the information is presented on a graphical user interface, as is provided in the illustrative example of FIG. 5. In one embodiment, the information is presented as text, such as in an e-mail message or text message. For example, the received subset of information may be in the form of a text message, and the portion of the subset presented comprises the text of the text message, which might say, "Patient Jane Doe: BP 140/80; Pulse 60 BPM; Blood Glu 400 MG/DL . . . " for example. In one embodiment, the presented information includes a time-stamp indicating the age or staleness of the information. For example "BP 140/80 (10:43 AM CST); Glu 400 MG/DL (8:05 AM CST); . . . ."

Turning now to FIGS. 4A and 4B, illustrative examples of user interface 180 are provided and referenced generally as 401 and 402, respectively. FIG. 4A depicts an embodiment of user interface 180 in the form of an electronic chart and FIG. 4B shows an embodiment as a display. In one embodiment, the user interface of FIG. 4B includes a touch screen, and in one embodiment, user interface of 4B includes other input means such as a keyboard, mouse, pad, voice-recognition module, or other means for receiving, from a user, an indication of information items. For example, in one embodiment, a user "checks" a checkbox adjacent to the information items for which he or she is interested in receiving updated information. In another embodiment, a user draws a box or loop around the information items of interest. In another embodiment, the user otherwise selects or provides an indication of information items of interest.

More specifically, in these illustrative examples, each of 401 and 402 depict a user interface presenting information about a third-party patient named Jane Mary Doe. Each of 401 and 402 has a user interface 180. In these embodiments of user interface 180, a user, such as a clinician or healthcare provider, can select those information items for which the user desires to receive updated information. The user is thereby subscribing to information related to the selected information items, here "Hypertension" and "Hyperglycemia." In one embodiment (not shown), the user may draw, with a finger, stylus, mouse, or similar input device, a circle or box around those information items for which the user wishes to subscribe, rather than selecting individual items. Following the receipt or a user's selection of information items, or after an indication of information items is received by a user or agent, user interface 180 may be used to present an encoded graphic image of a reference pointer, which points to a set of information items related to the selected information items, in one embodiment.

Figure 5:
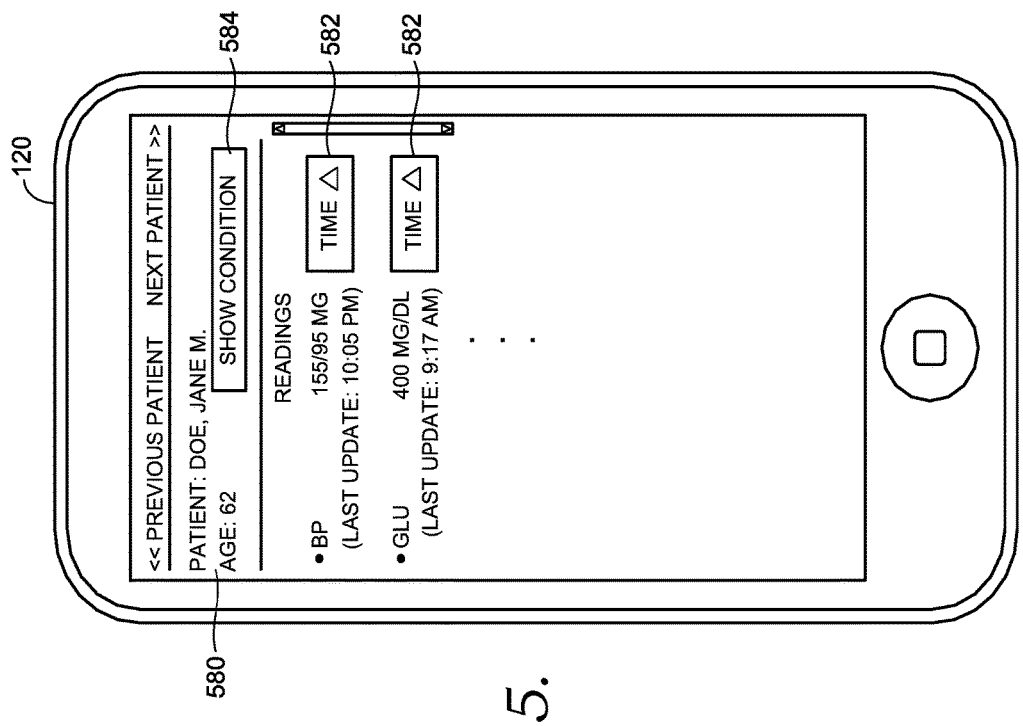
FIG. 5 depicts an example of a mobile device suitable for use in embodiments of the invention.

FIG. 5 illustratively shows an embodiment of mobile device 120. In the embodiment of FIG. 5, mobile device 120 includes a user interface 580, which can be a graphical user interface that is presenting a portion of a subset of information from a set of information related to one or more information items to which the user has selected or indicated. In one embodiment, the subset of information presented with user interface 580 is facilitated by way of an app running on mobile device 120. In the example depicted in FIGS. 4A and 4B, the user has subscribed to information relating to hypertension and hyperglycemia. User interface 580 depicts an example portion of a subset of information for which a user might be presented, with these subscriptions. Here, the subset of information includes information about blood pressure and blood glucose levels. In one embodiment, the app facilitates user authentication, subscription credentials and security. For example, the app communicates credential information to server 140 or subscription service 190 when requesting information associated with the reference pointer. In one embodiment, the app receives and validates user authentication, such as a password, voice-pattern recognition, or pictogram entered by the user, on mobile device 120, or finger-print or eye-scan using a camera on mobile device 120. This prevents an unauthorized possessor of the mobile device from accessing or viewing confidential third-party information, should the mobile device be stolen or used without permission. In one embodiment, mobile device 120 receives updates of information from the subset of information as the information becomes available or as it is communicated from subscription service 190 or server 140, but the app prevents a user from viewing the updated information until user authentication is received.

In one embodiment, user interface 580 also presents to the user information about the timeliness of the information item, if available. For example, in the embodiment shown in FIG. 5, user interface 580 shows a "Last Update: 10:05 p.m." adjacent to the information item for blood pressure. In one embodiment (not shown) user interface 580 also presents information about the time that the last update of information was received. In one embodiment, the mobile device maintains access to information about previously received updates, thereby allowing a user to view the changes in levels of a particular information item over time. For example, in the embodiment shown in FIG. 5, user interface 580 includes a "Time A" button such as Time-delta hotspot 582, adjacent to some of the information items, which when selected, touched, or pressed, enable a user to view the historical information about that information item. In one embodiment. For example, for the information item "BP" the user may see a chart listing Jane Doe's blood pressure for each of the previous updates received by the mobile device. In one embodiment, the previous update levels are presented as a graph, thereby enabling the user to more easily and quickly visualize changes in a patient's condition over time.

In some embodiments, user interface 580 contains functionality for receiving input from a user requesting additional information. For example, in the embodiment shown in FIG. 5, user interface 580 includes show-condition hotspot 584, which when selected, touched, or pressed, directs an app running on the mobile device to provide additional information about the patient's condition to the user via user interface 580. In one embodiment, the additional information includes information that is part of the subset of information already received on mobile device 120. In one embodiment, the additional information is requested from server 140 or subscription service 190.

In some embodiments, an app running on the mobile device may present to the user a button or option to "show more" information about the third party that the user is monitoring. In some embodiments, the user is provided a means to provide feedback based on the subset of information items received. For example, in one embodiment, the user can place orders or add comments or notes into the mobile device, via an app running on the mobile device. Such feedback may be securely communicated to server 140, in one embodiment.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A computing system comprising:
   one or more processors; and
   one or more computer-readable devices, coupled with the one or more processors, having computer-executable instructions embodied thereon that, when executed by at least one of the one or more processors, cause the server computing system to:
   receive, from a mobile device, an indication of one or more information items and authorization information;
   authenticate the ability of the mobile device to access the one or more indicated information items based on the authorization information;
   in response to successful authentication, determine the one or more information items based on the indication of one or more information items, and determine a set of information items that are related to and based on the one or more information items;
   monitor the set of information items to detect changes with respect to the set of information items; and
   provide, to the mobile device, an update to at least a subset of the set of information items based on a detected change to the set of information items.

2. The server computing system of claim 1, wherein the authorization information includes user credentials that identify the user.

3. The server computing system of claim 1, wherein the authorization information includes user credentials that specify information the user is permitted to access.

4. The server computing system of claim 1, wherein the authorization information includes subscription credentials that specify a period of time for which the user has access to the set of information items.

5. The server computing system of claim 4, wherein the subscription credentials are discretized to a per-information item level for the set of information items.

6. The server computing system of claim 1, wherein to authenticate the ability of the user to access the one or more indicated information items is further based on access-permission levels.

7. The server computing system of claim 1 wherein the server computing system is further caused to provide a notification to the mobile device that updated information is available.

8. A method for providing updates of secure information relevant to a mobile device comprising:
   receiving, from the mobile device, an indication of one or more information items and authorization information;
   authenticating the mobile device to access the one or more indicated information items based on the authorization information;
   in response to the authentication, determining the one or more information items based on the indication, and determining a set of information items that are related to and based on the one or more information items;
   monitoring the set of information items to detect changes with respect to the set of information items; and
   providing, to the mobile device, an update to at least a subset of the set of information items based on a detected change to the set of information items.

9. The method of claim 8, wherein the authorization information includes user credentials that specify information the user is permitted to access.

10. The method of claim 8, wherein the authorization information includes subscription credentials that specify a period of time for which the user has access to the set of information items.

11. The method of claim 10, wherein the subscription credentials are discretized to a per-information item level for the set of information items.

12. The method of claim 8, wherein authenticating the ability of the user to access the one or more indicated information items is further based on access-permission levels.

13. The method of claim 8 further comprising providing a notification to the mobile device that updated information is available.

* * * * *